(12) United States Patent
Schumann et al.

(10) Patent No.: US 7,070,966 B2
(45) Date of Patent: Jul. 4, 2006

(54) METHOD FOR OBTAINING POLYHYDROXYALKANOATES (PHA) AND THE COPOLYMERS THEREOF

(75) Inventors: Dirk Schumann, Taucha (DE); Roland Arno Müller, Markranstädt (DE)

(73) Assignee: UFZ Umweltforschungszentrum Leipzig-Halle GmbH, Leipzig (DE)

( * ) Notice: Subject to any disclaimer, the term of this patent is extended or adjusted under 35 U.S.C. 154(b) by 495 days.

(21) Appl. No.: 10/221,525

(22) PCT Filed: Mar. 13, 2001

(86) PCT No.: PCT/EP01/02801

§ 371 (c)(1),
(2), (4) Date: Nov. 26, 2002

(87) PCT Pub. No.: WO01/68892

PCT Pub. Date: Sep. 20, 2001

(65) Prior Publication Data

US 2003/0186398 A1     Oct. 2, 2003

(30) Foreign Application Priority Data

Mar. 14, 2000    (DE) ................... 100 13 514

(51) Int. Cl.
    *C12P 7/62* (2006.01)
(52) U.S. Cl. .................. 435/135; 528/179; 528/491
(58) Field of Classification Search ............ 435/135; 528/179, 491
    See application file for complete search history.

(56) References Cited

U.S. PATENT DOCUMENTS

| | | | |
|---|---|---|---|
| 3,275,610 A | 9/1966 | Coty | 260/80 |
| 5,871,980 A * | 2/1999 | Naylor et al. | 435/135 |
| 6,225,438 B1 * | 5/2001 | Green | 528/361 |
| 6,340,580 B1 * | 1/2002 | Horowitz | 435/135 |
| 6,709,848 B1 * | 3/2004 | Martin et al. | 435/134 |
| 6,737,263 B1 * | 5/2004 | Dragotta et al. | 435/262 |

FOREIGN PATENT DOCUMENTS

| | | |
|---|---|---|
| DE | 27 01 278 | 7/1977 |
| DE | 229 428 A1 | 11/1985 |
| DE | 196 23 778 A1 | 12/1997 |
| DE | 693 11 738 T2 | 1/1998 |
| DE | 694 07 177 T2 | 5/1998 |
| DE | 196 19 084 C2 | 8/1998 |
| DE | 197 12 702 A1 | 10/1998 |
| DE | 195 33 459 C1 | 11/1998 |
| EP | 0 014 490 A1 | 8/1980 |
| EP | 0 015 123 A1 | 9/1980 |
| EP | 0 015 669 A2 | 9/1980 |
| EP | 0 58 480 A1 | 8/1982 |
| EP | 0 069 497 A2 | 1/1983 |
| EP | 0 124 309 | 11/1984 |
| EP | 0 145 233 A2 | 6/1985 |
| EP | 0 149 744 A1 | 7/1985 |
| EP | 0 304 293 A2 | 2/1989 |
| KR | 9502866 | 3/1995 |
| WO | WO 94/10289 | 5/1994 |
| WO | WO 97/17459 | 5/1997 |

OTHER PUBLICATIONS

Abstract of KR 9502866 Mar. 27, 1995.

* cited by examiner

*Primary Examiner*—Herbert J. Lilling
(74) *Attorney, Agent, or Firm*—Norris McLaughlin & Marcus PA

(57) ABSTRACT

The invention relates to an enzymatic-chemical method for obtaining polyhydroxyalkanoates (PHA), especially polyhydroxybutyrate (PHB), or the copolymers thereof, from biomass. The inventive method comprises chemically treating the biomass with a reducing agent that reduces the non-PHA cell components of the biomass. The chemical treatment is carried out before and/or after enzymatic cell disruption. The inventive method allows, unlike other cell disruption techniques, for obtaining polyhydroxyalkanoates from biomass with a relatively low PHA content (for example <60%) without drastically changing or deteriorating the polymer properties or polymer purity.

12 Claims, 1 Drawing Sheet

METHOD FOR OBTAINING POLYHYDROXYALKANOATES (PHA) AND THE COPOLYMERS THEREOF

BACKGROUND OF THE INVENTION

The invention relates to and enzymatic-chemical method for obtaining polyhydroxylalkanoates (PHA), especially polyhydroxybutyrate (PHB), or the copolymers thereof, from biomass. The inventive method comprises chemically treating the biomass with a reducing agent that reduces the non-PHA cell constituents of the biomass. The chemical treatment is carried out before and/or after enzymatic cell disruption. The inventive method, unlike other cell disruption techniques, makes it possible to obtain polyhydroxyalkanoates from biomass with a relatively low PHA content (for example <60%) without drastically changing or degrade the polymer properties or polymer purity.

Various methods are known for the microbial production of PHA polyesters, with the best-known representative being polyhydroxybutyrate (PBH), and/or for the production of PHA copolymers, which are disclosed in the number of documents describing the present state of the technology, since PHB and other PHA have an increasing economical importance as polymers with thermal-plastic properties that can be completely biologically decomposed. For example, EP 0 015 669 A2 describes the microbial production of PHB from methanol, while the extraction of copolymers is disclosed, for example, in EP 0 304 293 A2 and EP 0 069 497 A2. For example, glucose/propionic acid are used as a substrate mixture.

Other methods for obtaining PHB with a good yield coefficient and saccharose as a substrate are disclosed, for example, in EP 0 149 744 A1, while methods for producing PHB and copolymers thereof are disclosed in DE 196 19 084 C2.

According to the present state-of-the-art, PHA-containing biomass is processed either by extraction of a dried biomass with corresponding PHB/PHA solvents, chemically by addition of cell-destroying substances or enzymatic.

The chemical extraction is generally performed with halogenated solvents. Used are solvents that are capable of dissolving large quantities of PHA (for example chloroform) or solvents that can be used to obtain very pure PHA, since only small quantities of other cell constituents dissolve in those solvents (for example in dichloroethane). For example, EP 0 15 669 A2 discloses various methods for destroying cells and subsequently extracting PHB from destroyed cells by halogenated hydrocarbons (for example, chloroform, dichloromethane, 1,2-dichloroethane and 1,2-dichloropropane). The use of halogenated solvents is also described in other references (for example, in U.S. Pat. No. 3,275,610 chloroform; 1,2-dichloroethane in EP 0 014 490 A and EP 0 015 123 A).

In order to avoid the halogenated solvents which pose health risks, other methods using safer solvents have been developed. For example, the use of cyclic carbonic acid esters (U.S. Pat. No. 410,533) or of ethyl- and/or methyl lactate (DE 27 01 278 A1, DE 195 33 459 C1 and DE 196 23 778) are known. Also disclosed is the use of acetic acid or acetic anhydride as solvents (DE 197 12 702 A1, DD 229428 A1).

The individual process steps for PHA extraction can be described as follows:

The microbial biomass is initially separated from the culture liquid by filtration, separation or centrifugation (as long as this is not a genetically modified plant biomass), followed—depending on the efficiency—by an optional mechanical cell disruption (e.g., by using a ball mill) for increasing the extraction yields. The biomass can be dried, for example, by freeze-drying or spray-drying. PHB, PHA and/or their copolymer are extracted from the dried biomass using suitable extraction means. The purity of the extracted polymers can be increased by pre-extractions of the dried biomass using solvents that do not dissolve the polyesters.

For example, EP 0 124 309 A1 describes pre-extraction of the biomass with acetone, whereas methanol is used in EP 0 058 480 A1.

Typically, in addition to the frequently required pre-extractions, large quantities of extraction agents have to be used due to the generally relatively poor solubility of PHB and in particular of the so-called short-side-chain (ssc) PHA. Separation of the highly viscous polymer solution from the remaining cell constituents poses additional problems.

Moreover, many of the employed PHB-/PHA-solvents, in particular the halogenated solvents, are suspected to pose health risks. The use, handling and storage of large quantities of solvents usually also poses an economical and also ecological problem.

For this reason, methods have been developed which operate either without any solvents or only with small quantities of solvents. With these methods, the polymer granules are not physically dissolved, but the so-called NPCM cell constituents (non-PHA cell matter), with exception of the intracellular granules, are rendered chemically or enzymatically water-soluble as much as possible. The granules can then be separated from the aqueous solution by conventional methods.

Among one of the oldest known methods for PHB and PHA extraction is, for example, the chemical cell disruption with hypochloride. With this method, almost all cell constituents, with the exception of the polymer granules, are destroyed by oxidation. However, the method has also disadvantages. Although this method leaves the outer shape of the granules intact, the macromolecules are partially damaged. This method is restricted to a small-scale laboratory environment both as a result of the severe reduction of the molar mass of the polymers as well as the release of hazardous waste water.

Another oxidation method is described in DE 694 07 177 T2. PHA is obtained, in particular from polyhydroxybutyrate-hydroxyvalerate copolymers (PHBHV), either with hydrogen peroxide (preferably) or with peracetic acid, perborate, percarbonate and/or with chlorine or chlorine-containing oxidation agents in the presence of chelate formers. The effect of the oxidation agents, in particular of peroxides, on the PHA production is described in detail in EP 669 970 A2.

With the oxidizing methods, however, not only are undesirable cell constituents, such as nucleic acids and cell wall polymers, decomposed, but the average molar mass of the PHA polymers is also undesirably reduced. Accordingly, PHB/PHA cannot be obtained in this way without degrading the quality of the desired polymer material. This is particularly disadvantageous with biomasses having a small PHA content, since the smaller the PHA content, the more has to be oxidized and the more likely damage to the polyester occurs. In addition, radicals (e.g., on the methine carbon of a poly-□-hydroxyalkonoate) can form that cross-link the macromolecules. This partial cross-linking reduces the solubility in the PHA solvents to a point where the polymer is only able to swell. Cross-linking has an adverse effect in applications where the polymer solution needs to be post-processed. In addition, partial cross-linking reduces the biological decomposability, the biological reabsorption as well as the bio-compatibility and therefore weakens important properties of the polyhydroxyalkonoates.

Known methods that avoid these disadvantages lyse the undesirable cell constituents with the help of enzymes. For example, EP 0 145 233 A2 describes using proteolytic enzymes, in part in cooperation with a phospholipase and/or with surfactants. In a method described in DE 693 11 738 T2, proposes to combine the application of heat, possibly nuclease, proteolytic enzymes and/or phospholipases and/or lysozyme, chelate formers, surfactants and oxidizing post-treatment and/or solvent re-precipitation. KR 9502866 proposes to use only, for example, pre-extraction agents, such as hot water or acetone as well as a protease under strongly alkaline conditions.

The microorganisms employed in the aforedescribed enzymatic cell disruptions [mainly *Rastonia eutrophus* (formerly: *Alcaligenis eutrophus*), *Alcaligenis latus*, various *pseudomonas* strain and the like] are known as PHA producers with a high PHA content—approximately 60–80% in dry mass, and these methods were frequently developed more or less dependent on the employed microorganisms. It is known that the polymer granules can be easily isolated, for example using just a few steps, from microorganisms with a relatively high PHA content or specific lytic properties. It is often sufficient to use between one and two enzymes, surfactants and possibly chelate formers to extract the polymers. Sometimes, an oxidizing process is sufficient to achieve a purity of between 90 and approximately 98%, in particular when microorganisms can be used that already in the initial stage have a relatively high PHA content, for example 70–80%.

The extraction of PHA from biomass with a smaller PHA content of, for example, 30–60% requires the more complex process (i.e., more steps). The complexity increases with decreasing PHA content of the biomass. The methods known today are either not suitable at all or only in a limited fashion for extracting PHA from microorganisms with low PHA content.

It has been observed that the customary, immediate cell wall lysis in a first step (for example with lysozyme) does not necessarily offer the best possibility to wash out the NPCM fraction of the biomass. This applies particularly to PHA producers with a low PHA content. A frequently observed incomplete lysis and agglomeration of the biomass, including the PHA, can then make additional purification of the PHA granules significantly more difficult as a result of the inclusion of impurities.

The capability of the microorganisms to accumulate for high PHA content has been of primary interest in their selection for PHA extraction. The areas of application have changed from previously emphasized mass production to today's specialized products made from PHA, so that nowadays a microorganism with a relatively low polymer content may be preferred because it provides different advantages. For example, such advantages may be excellent mechanical properties of the PHA, high molar mass and the like, as well as a rapid, cost-effective culturing of the strain (e.g., no sterilization of the apparatus is required, etc.).

SUMMARY OF THE INVENTION

It was therefore an object of the invention to provide a simple and reliable method for extracting PHA homo- and copolymers from biomass, in particular from biomass with smaller PHA content, which does not use PHB/PHA solvents or uses these solvents only in small quantities, and which practically eliminates health risks for the operator and/or environmental hazards. Nevertheless, the quality and yield of the extracted PHA should be comparable at least to that obtained with known extraction processes.

The object of the invention is solved by a method for enzymatic extraction of homo- and copolymers of polyhydroxyalkanoates (PHA) from biomass, wherein the biomass is treated before and/or after the enzymatic decomposition at least once with a reducing agent which reduces the non-PHA cell constituents of the biomass.

Accordingly, a chemical-enzymatic method can be used to obtain the PHA from a biomass with a high yield and good quality, even if the PHA content of the biomass is relatively small, for example contents of <60%. It is thereby unimportant when the reducing agent(s) according to the invention is/are added. Surprisingly, the reducing agent(s) significantly reduce(s) the non-PHA cell constituents (NPCM) of the biomass and thereby increase(s) the PHA content. The treatment with the reducing agent can be performed before, between or after the enzymatic decomposition. In the context of the present invention, reducing agents are to be understood as chemical substances which have the ability to separate and decompose proteins, nucleic acids and polysaccharides (cell wall separation). Optionally, the reducing agents can be used in combination with tensides and/or complex formers.

DETAILED DESCRIPTION OF THE PREFERRED EMBODIMENT

Figure 1:
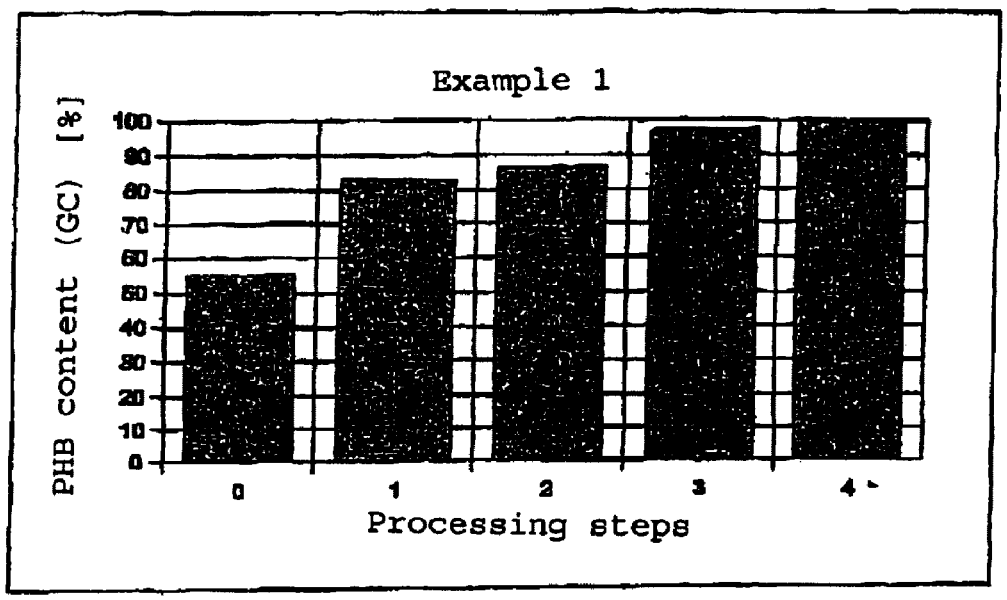
FIG. 1 is a graph showing the increase in the concentration of PHB during processing, for Example 1.

According to a preferred embodiment of the invention, a dithionite salt, a disulfite salt, phosphorous acid and/or a hydroxyl ammonium compound are used, for example, sodium dithionite, sodium disulfite or a hydroxyl ammonium chloride compound. According to the invention, preferably dithionite is used as a reducing agent.

The method of the invention is described in more detail below, wherein the order of the individual steps can be interchanged. For example, the step referred to as method step 3 can be carried out before step 2, or step 1 can be repeated after step 3. Moreover, if necessary other steps can be repeated or omitted. The arrangement in time depends on the biomass and/or its PHA content, as well as on the subsequent application and the desired purity of the PHA.

Important for the invention is that the chemical treatment of the biomass for removing NPCM is performed at least once, as described in process step 1.

In a preferred embodiment of the invention, the biomass is pre-treated before the biomass is actually decomposed by chemical-enzymatic decomposition with the goal to increase the formation of agglomerates to speed up and facilitate separation of the biomass from the culture liquid by sedimentation, filtration, separation and/or centrifugation. The selection of this separation methods is substantially independent of the employed microorganism.

According to the present invention, an agglomeration is achieved by shifting the pH value of the biomass by acidifying below the original value, in any case below the neutral point into the acidic range. Optionally, enzymatic decomposition is already performed during the pre-treatment.

Preferred are pH values from 1 to 6.5, preferably a pH value of 1 to 5.5, in particular from 1–4. Exposing the biomass suspension for a short-time, i.e., for 5 to 60 minutes, to higher temperatures between 30 and 140° C., preferably between 30 and 90° C., advantageously helps to increase the particle size. In another embodiment for agglomeration, the pH value of the biomass is briefly adjusted for maximal 5–30 minutes to between 7 and 12 before acidification, during which time the temperature is adjusted stepwise between 30 and 140° C. Particularly preferred is a pH value between 8 and 9.

For increasing agglomerate formation in the biomass and for simultaneously causing damage to the cell walls and reducing the protein content, additional chelate formers and/or proteolytic enzymes can optionally be employed. Particularly advantageous is the simultaneous application of pepsin when flocculating microorganisms in an acidic environment.

Subsequently, the still solid, flocculated biomass components are separated from the liquid in a conventional manner. This can be done, for example, by filtration, separation, centrifugation or sedimentation, for example in a baffle plate thickener.

Process Step 1:

If the biomass is present in form of a solid moist biomass or dry biomass, the biomass is diluted with water until the obtained suspension can be stirred. An effective reduction of the non-PHA cell constituents is achieved by reacting the biomass with suitable chemical reducing agents. Theoretically, these can be all reducing agents which can be used in an aqueous medium and that do not damage or contaminate the PHA, i.e., dramatically degrade its properties. Particularly preferred according to the present invention is the use of a dithionite salt, preferably sodium dithionite, which (partially) reduces non-PHA cell constituents and/or promotes their hydrolysis. Surprisingly, the significant reduction of the non-PHA cell constituents is greater than would be respected as a result of the chemical reduction of certain functional groups.

Depending on the type of the biomass and its PHA content, 1–200 g, preferably 10–100 g, particularly preferred 20–80 g, dithionite salt per kilogram dry biomass are used. The method using dithionite salt is carried out under neutral to alkaline conditions, preferably at pH values of 7 to 10, particularly preferred are pH values of 8 to 9. Temperatures between 20 to 110° C., preferably between 40 to 90° C., are advantageous.

Additional agents, such as chelate formers and/or tensides, can be added to destabilize the cell walls. Suitable chelate formers are, for example, EDTA (ethylene diamine tetra acetic acid), 1, 2-bis (2-aminoethoxy)-ethane-N, N,N', N'-tetra acetic acid, nitrilotriacetic acid, citric acid, tartaric acid, polyphosphate and the like. The employed tensides are preferably non-ionic or anionic tensides.

After this treatment, the suspension of PHA, raw-PHA or PHA-containing biomass is separated in a conventional manner (for example, by centrifugation or (cross-flow) filtration) from the liquid, which now contains the solubilized non-PHA cell constituents. Thereafter, the PHA-containing moist mass is washed in at least one step or in several steps with hot deionized, tenside-containing water having a temperature of preferably 40 to 100° C., more preferably 60 to 80° C., until solubilized non-PHA cell constituents are no longer washed out.

Method Step 2 (Optional, Depending on Residual Content of Non-PHA Cell Constituents and Purity Requirements—Can Also be Step 1):

For further solubilizing of non-PHA cell constituents, the moist mass is re-suspended and treated with proteolytic enzymes. Pancreatine or the individual enzymes contained therein, trypsin, chymotrypsin, as well as papain, bromelain, ficin, rennin, subtilisin and the like and mixtures thereof, can be considered as long as no significant mutual decomposition occurs. Advantageously, esterases, such as (triacylglyceryl-) lipase(s), either as a component of the pancreatin mixture or as an individual enzyme and/or other esterases, also be used as long they do not cleave the ester binding of the PHA. This also facilitates solubilization of fats and lipids, especially the lipopolysaccharide component of the cell wall gram-negative bacteria. For removing the released fatty acids, the suspension is mixed with suitable tensides. After this treatment, the particles are separated from the liquid in a conventional manner and the obtained moist mass is washed at least once or several times with deionized, tenside-containing water.

Method Step 3 (Optional, Depending on the Residual Content of Non-PHA Cell Constituents and Purity Requirements):

The moist mass or its suspension is treated with lysozymes, such as mureinase, to remove the (partially) remaining peptidoglycan, and optionally also with cellulases to aid in cleaving the □-1,4 bond. After the treatment, the particles are separated from the suspension and the moist mass is washed, as described above. If not already performed in a previous step, the obtained PHA is dried in a conventional manner. If the PHA content is sufficiently high, drying is relatively fast due to the hydrophobic properties of the PHA and can already be observed at room temperature.

Method Step 4 (Optional, Depending on the Residual Content of Non-PHA Cell Constituents and Purity Requirements):

If necessary, the dried mass of PHA granules is post-purified with non-PHA solvents for optionally removing residual impurities, in particular lipids. Particularly suited for this purpose are alcohols, such as methanol, ethanol or propanol, ketones, such as acetone or ethylmethyl ketone, ester such as methyl- and ethyl acetate, as well as alkanes such as pentane, hexane, heptane and/or mixtures of the aforedescribed solvents and/or mixtures with water.

An alternative method for post-purification is re-precipitation of the PHA with PHA solvents, wherein the PHA solution is first purified, for example by filtration, to remove insoluble contaminants.

The already obtained relatively pure PHA can also be purified in an additional step by once again treating the PHA with the reducing agent, for example dithionite.

The major advantage of the method of the invention is the simplified separation of the biomass from the culture liquid by an optional pre-treatment (agglomeration) and the sedimentation of the (partially decomposed) microorganisms and/or polymer granules, as well as the immediate post-treatment without requiring a lengthy drying step—which is frequently necessary with solvent extraction—during processing. In addition, the mechanical cell disruption is replaced by the substantially shorter and more effective chemical-enzymatic treatment. The efficient reduction in the non-PHA cell constituents from the biomass by the chemical step, especially in conjunction with enzymatic steps, should be emphasized. Particularly Surprising was the noticeable decrease in the non-PHA cell constituents as a result of the chemical step, without serious degradation in the quality of the polymer properties. Accordingly, the method is particularly advantageous for recovering PHA from biomass with a relatively small PHA content.

The obtained yields are significantly greater than those obtained with conventional PHA extraction agents, because the cell mass with the polyesters essentially remains always in the same containers, so that the loss of material is small. With the method of the invention, at least approximately 75%, preferably more than 95% of the PHB and/or its copolymers that are present in the biomass can be recovered.

The health risk associated with the method of the invention can also be considered to be very small, especially in comparison with an extraction using (halogenated) extraction agents, which have been shown to cause liver damage and even cancer. The environmental risks can also expected to be quite small, because the solvent is mainly water. The chemicals and enzymes are only used in relatively small quantities and are essentially biologically degradable. Solvents employed for an optional post-extraction are relatively non-toxic and can be recycled.

The invention will be described hereinafter in more detail with reference to certain embodiments, without being limited thereto:

EXAMPLE 1

Recovery of PHB From a Methylocystis Biomass

As stirred tank discharge, 6.5 liters of a suspension of the PHB producer methylocystis spec. GB 25 which has been condensed by separation and having a biomass concentration of 138.5 g/l are used (i.e., in total 900 gram dry biomass). The PHB content at the beginning was 55.3%, referenced to dry biomass. The PHB was recovered in a conventional double wall reaction vessel with a stirrer.

In step 1, the PHA value of the suspension was increased from initially 5.1 to 8.5 using soda lye. 1.8 g (0.2% referenced to dry biomass) of a non-ionic tenside and 4.5 g (0.5%) ethylenediaminetetraacetic acid sodium salt were added. Finally, 90.0 g (10.0%) sodium dithionite (with iodometrically measured 87% dithionite content) were added and heated in an inert atmosphere in one hour from 20° C. to 80° C. while stirring. After half an hour at 80° C., the suspension was cooled to 60° C. and centrifuged warm (approximately 20,000×g). The pellets of the moist mass were then re-suspended in demineralized water and again centrifuged. The moist mass which has been washed once in this manner, was again re-suspended to the original volume for step 2.

The PHA value was checked in step 2, and had as required a value of 8.5. The slightly alkaline conditions are important for achieving the pH-optimum of the subsequently added enzyme mixture triacylglyceryle lipase (1.8 g or 0.2%) and pancreatin (1.8 g or 0.2%). For this purpose, 1.8 g non-ionic tenside was again added. The reaction lasted 12 h under constant stirring and in an inert gas at 40° C. Thereafter, the particles are again separated by centrifugation, washing, and re-suspension to the initial volume.

In step 3, the pH value is lowered with diluted sulfuric acid from now 7.5 down to 5.0 and 1.8 g (0.2% referenced to the dry biomass) of lysozyme (mureinase) are added. The reaction lasted 4 h at 40° C. under constant stirring and in an inert atmosphere. Subsequently, 1.8 g papain was added and the suspension remained at 60° C. for 2 h. At the end, centrifugation and 3 additional washings with deionized water were performed. For drying at room temperature, the PHB moist mass is spread out flat. The PHB obtained in this manner still contained impurities, in particular free fatty acids (analysis with GC-MC), which can be removed by post-extraction with the non-PHB solvent ethyl acetate (step 4). A total of 472 g PHB was obtained with a yield of approximately 95%. An average value of 99.5% for the purity of the PHB was obtained by gas chromatography at the end of processing.

FIG. 1 shows the increase in the concentration of PHB during processing. The effect of the chemical addition of dithionite according to the invention is clearly visible.

| Step | Description |
|---|---|
| Pre-treatment | 6.5 l suspension with 900 g dry mass M. spec. GB 25: PHB content: 55.3% |
| 1 | chemical step with dithionite, tenside, chelate former: PHB content: 82.9% |
| 2 | 1. enzymatic step with lipase and pancreatin: PHB content: 86.2% |
| 3 | 2. enzymatic step with lysozyme and papain: PHB content: 97.1% |
| 4 | post-extraction of the PHB with ethyl acetate: PHB content: 99.5% |

EXAMPLE 2

Recovery of PHB From a Paracoccus Biomass

As stirred tank discharge, 15 liters of a suspension of the PHB producer paracoccus denitrificans which has been condensed by separation was used. The total dry biomass was 5848 g, corresponding to a biomass concentration of 390 g/l. The PBH content at the beginning was 54.0%, referenced to the dry biomass. The PBH was again recovered in a double wall reaction vessel with stirrer.

In step 1, the pH value of the suspension was increased from initially 4.8 to 8.5 with soda lye. 11.5 g (approximately 0.2% referenced to the dry biomass) of a non-ionic tenside and 30.0 g (0.5%) ethylene diamine tetraacetic acid—sodium salt was added. Finally, 180.0 g (3.0%) sodium dithionite was added and heated in an inert atmosphere for one hour from 20° C. to 80° C. under stirring. After half an hour at 80° C., the suspension was cooled to 60° C. and warm centrifuged (approximately 20,000×g). Thereafter, the pellets of the moist mass were re-suspended in demineralized water, followed by another centrifugation. The moist mass which had been washed in this way once, was re-suspended to the original volume for step 2.

The pH value was checked in step 2 and adjusted again from 7.2 to 8.5 by adding soda lye. Like in example 1, the enzyme-tenside mixture of triaxylglyceryl lipase, pancreatin and tenside was added. The reaction lasted 12 h in an inert gas at 40° C. under stirring. Thereafter, the particles were again separated by centrifugation, washing, and the re-suspension to the initial volume.

In step 3, the PHA value of the suspension was reduced to 5.5 using sulfuric acid, and lysozyme was added. The reaction lasted for 4 h at 40° C. in an inert gas under stirring. Subsequently, papain was added and the suspension was left for 2 h at 60° C. As in example 1, step 3 was concluded by centrifugation and 3 washes with deionized water. The obtained PHB mass was spread out flat and dried at room temperature. As in example 1, the PHB also included impurities, such as free fatty acids and indole compounds (GC-MS analysis), which were removed by post-extraction with ethyl acetate (step 4). A total of 2653 g PHB was obtained with a yield of approximately 85%.

Figure 2:
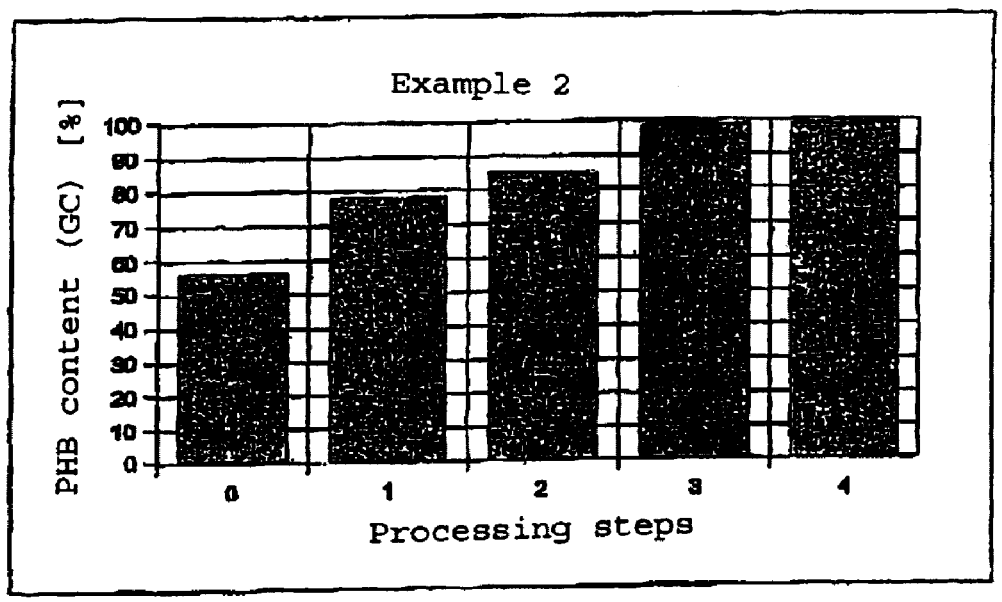
FIG. 2 is a graph showing the increase in concentration of PHB during processing, for Example 2.

FIG. 2 shows the increasing concentration of PHB during processing. The effect of the chemical addition of dithionite according to the invention is also evident.

| Step | Description |
|---|---|
| Pre-treatment | 15 l after flocculating with 2000 g dry mass M. spec. GB 25: PHB content: 56% |
| 1 | chemical step with tenside, chelate former, dithionite: PHB content: 78% |
| 2 | 1. enzymatic step with lipase and pancreatin: PHB content: 85% |
| 3 | 2. enzymatic step with lysozyme and papain: PHB content: 98.7% |
| 4 | post-extraction of the PHB with ethyl acetate: PHB content: >99% |

COMPARATIVE EXAMPLE 3

By only oxidizing with hydrogen peroxide under alkaline conditions similar to DE 694 07 177 T2, only 80% raw-PHB was obtained from generally available PHA producers with an average PHB content of 45%.

Likewise, stepwise enzymatic treatment with three proteolytic enzymes (papain, pepsin, bromelain), tensides and chelate formers, as well as a subsequent treatment with a mureinase produced only a maximum PHB content of 88%.

EXAMPLE 4

Washing Out NPCM (Non-PHA Cell Matter) and Increasing the PHB Content of a Methylocystis-Biomass with Relatively Small PHB Content Using the Reducing Agents of the Invention A suspension of the PHB producer methylocystis spec. GB 25 that had been condensed by centrifugation, washed with demineralized water, then again condensed and subsequently freeze-dried was used as biomass. PHB formation in the cells took place under sulfate-deficient conditions; the PHB content was at the beginning 34%, referenced to dry biomass.

In each of 5 experiments, 30.00 g of this biomass was re-suspended in 150 ml demineralized water and the pH value of the suspension was increased from initially 4.5 to 8.5 with his soda lye. The first biomass preparation (RED 0) was then placed in a nitrogen atmosphere and subsequently heated for one hour to 85° C. After the treatment, the biomass was centrifuged from the suspension for 30 minutes at approximately 20,000×g, again re-suspended in demineralized water, once more centrifuged, i.e., washed once, and the biomass pellet was finally frozen in a collarless centrifuge beaker at −17° C. For the second experiment (RED 1), 2.45 g sodium dithionite salt (12.375% dithionite per NPCM; with iodometrically measured 87% dithionite content) was also added to the biomass before heating in the nitrogen atmosphere, with all other steps being performed as described above.

In the other experiments, quantities (of the effective principle) of sodium disulfite, phosphorous acid and/or hydroxyl ammonium chloride that were equimolar to the dithionite were added.

The frozen biomass pellets of the experiments were always removed from the centrifuge beakers as a single piece, freeze-dried and checked for PHB content and/or if NPCM had washed out.

| Experiment | Additive | PHB content of the dry biomass (%) after additive and 1 h at 85° C. in an inert gas atmosphere |
|---|---|---|
| RED 0 | None | 35 |
| RED 1 | sodium dithionite | 41 |
| RED 2 | sodium dithionite | 41 |
| RED 3 | phosphoric acid | 40 |
| RED 4 | Hydroxyl ammonium chloride | 41 |

The table illustrates advantage of using reduction agents according to the invention.

The invention claimed is:

1. Method for enzymatic extraction of homo- and copolymers of polyhydroxyalkanoates (PHA) from biomass, comprising the steps of (a) enzymatically decomposing the biomass and before and/or after step (a), treating the biomass at least once with an agent which reduces non-PHA cell components of the biomass.

2. Method according to claim 1, wherein the agent is chosen from the group consisting of a dithionite salt, a disulfite salt, phosphorous acid and a hydroxyl ammonium compound.

3. Method according to claim 1, wherein the process takes place at the pH value of 7 to 10 and a temperature of 20 to 110° C.

4. Method according to claim 1, further comprising the step of pretreating the biomass to be decomposed for increasing the formation of agglomerates.

5. Method according to claim 4, further comprising the step of changing the pH value of the biomass into the acidic range in order to effect agglomerate formation.

6. Method according to claim 1, further comprising the steps of removing residual impurities, and post-extracting the extracted PHA with solvents that do not dissolve PHA.

7. Method according to claim 1, wherein the chemical and enzymatic treatment and optionally the pre-treatment is performed in a reaction vessel.

8. Method according to claim 1, wherein the biomass has a starting PHA content of <60 wt. %.

9. Method according to claim 2, wherein the agent is dithionite.

10. Method according to claim 5, wherein the pH is changed to 1–6.5.

11. Method according to claim 6, wherein the solvent is chosen from the group consisting of water, alcohols, ketones, esters, alkanes and mixtures thereof.

12. Method according to claim 6, further comprising the step of re-precipitating the PHA with PHA solvents.

* * * * *